United States Patent [19]
Levine

[11] Patent Number: 5,943,473
[45] Date of Patent: Aug. 24, 1999

[54] HEATED CARTRIDGE HUMIDIFIER

[76] Inventor: Walter Levine, 6528 N. Nokomis, Lincolnwood, Ill. 60646

[21] Appl. No.: 08/865,439

[22] Filed: May 29, 1997

[51] Int. Cl.⁶ .............................. F22B 1/28; A61M 15/00
[52] U.S. Cl. ...................................... 392/401; 128/203.16
[58] Field of Search ..................................... 392/386, 394, 392/396, 400, 401, 402, 403; 128/203.16, 203.17, 203.26, 203.27; 261/139, 142, DIG. 65

[56] References Cited

U.S. PATENT DOCUMENTS

| | | | |
|---|---|---|---|
| 3,659,604 | 5/1972 | Melville et al. | 392/403 |
| 4,036,919 | 7/1977 | Komendowski et al. | 392/405 |
| 4,203,027 | 5/1980 | O'Hare et al. | 128/203.27 |
| 4,926,856 | 5/1990 | Cambio, Jr. et al. | 128/203.06 |
| 5,195,515 | 3/1993 | Levine . | |

Primary Examiner—Teresa Walberg
Assistant Examiner—Sam Paik
Attorney, Agent, or Firm—Greer, Burns & Crain, Ltd.

[57] ABSTRACT

An improved heated cartridge humidifier for delivering humidified respiratory gases to patients. A humidifier housing includes a gas and water supply and a gas outlet. A humidifier base plate engages a heating element. The base plate includes a central heat conductive portion retained in an outer insulating portion which prevents the lateral dissipation of heat received from the heating element. The baseplate enhances the heat transfer to the water, and therefore, enhances the humidity of the gases.

15 Claims, 3 Drawing Sheets

HEATED CARTRIDGE HUMIDIFIER

BACKGROUND OF THE INVENTION

The present invention relates generally to devices for delivering gases having a controlled vapor level and temperature to a delivery point, and more particularly to humidifier devices employing disposable humidifier cartridges which receive water from an adjacent container.

When a normally healthy person breathes atmospheric air, his air passages supply heated moisture to the inhaled gases, with the body being able to supply the required amount of heat and moisture. However, when subject to certain medical conditions, the patient's mechanism of supplying heated moisture is disrupted, and it becomes necessary to provide an artificial system for warming inspired gases to a point at or near normal body temperature before the gases are delivered to the patient. Accordingly, it is desirable to humidify the inspired gases to a level at or near full (100%) moisture saturation.

Conventional systems for providing heated and moisturized respiratory gases basically fall into two groups; nebulizers, which produce aerosols of fine water droplets, and heated humidifiers, which supply heat and moisture to a gas by the passage of the gas through or over a heated water bath or evaporated surface. The present invention is concerned with the heated humidifiers.

One such humidifier system includes a rigid, refillable water container designed to be placed upon a base unit having a heating element and is disclosed in U.S. Pat. No. 5,195,515 to Levine. This system includes a disposable heated cartridge humidifier for use with a collapsible water supply container and a heating device. The cartridge housing has a base plate fabricated from a conductive material such as metal, preferably aluminum. Included on the base plate is a peripheral lip which is crimped over a flange of a lower end of the housing.

One problem with this arrangement is the difficulty in controlling the inherent variation in the crimping action during assembly to prevent leakage between the housing and the base plate. Also, in the prior cartridge humidifier, the transfer of heat between the base plate and sidewall of the housing is a less than optimum arrangement for the humidification of the respiratory gases because heat from the base plate is laterally dissipated to the sidewalls of the housing and into the ambient air.

Another drawback of conventional heated cartridge humidifiers is that the incoming air is not given sufficient opportunity to be mixed with the water for full humidification, and thus is forced from the cartridge lacking adequate humidity.

Accordingly, it is the primary object of the present invention to provide an improved heated cartridge humidifier with a leak proof seal between the humidifier housing and the base plate.

It is another object of the present invention to provide an improved heated cartridge humidifier with a base plate which provides for improved heat conductivity from the heating element to the water in the cartridge.

It is a further object of the present invention to provide an improved heater cartridge humidifier in which incoming air is introduced into the cartridge in close proximity to the water supply to facilitate humidification of the air.

It is yet another object of the present invention to provide an improved heater cartridge humidifier which can be economically manufactured so as to be a disposable unit.

SUMMARY OF THE INVENTION

The above identified objects are met or exceeded by the present improved heated cartridge humidifier. A humidifier housing has inlets for breathable gases and water, and an outlet for the humidified gases. A separate heating element provides the heat required to evaporate the water and humidify the gases passing through the housing. A base plate of the housing engages the heating element. The base plate includes a central heat conductive portion and an outer insulating portion to prevent lateral dissipation of the heat received from the heat source to the sidewall of the housing. Another feature is that an inlet of the humidifier cartridge extends deeply into the cartridge to promote humidification of the incoming breathable gas.

More specifically, a heated cartridge humidifier includes a humidifier housing configured to operationally engage a separate heat source. The housing has a sidewall with an open lower end portion and an integrally formed closed upper end portion, a breathable gas inlet, a water inlet, and a humidified gas outlet. A base plate of the housing is configured for being sealingly engaged to the open lower end of the housing. Included on the base plate is an insulating portion and a conductive portion. The insulating portion sealingly retains a perimeter of the conductive portion and provides an attachment point for the base plate to the housing. The conductive portion is configured to efficiently transfer heat received from the heat source to the water received from the water inlet and, therefore, humidify the breathable gases.

DETAILED DESCRIPTION OF THE INVENTION

Figure 1:
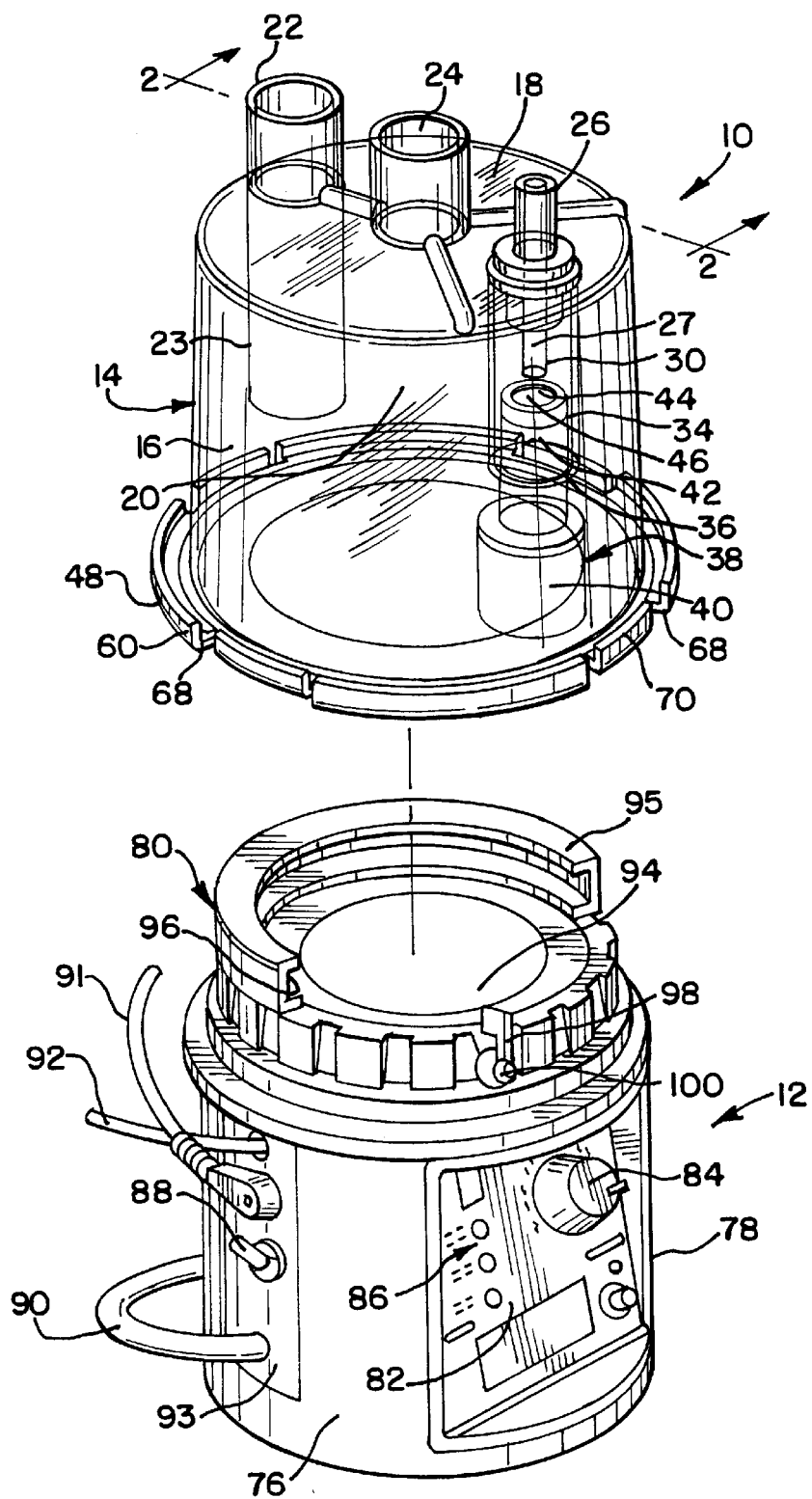
FIG. 1 is partially exploded perspective view of the improved heated cartridge humidifier and heat source, with some parts omitted for clarity.
Figure 2:
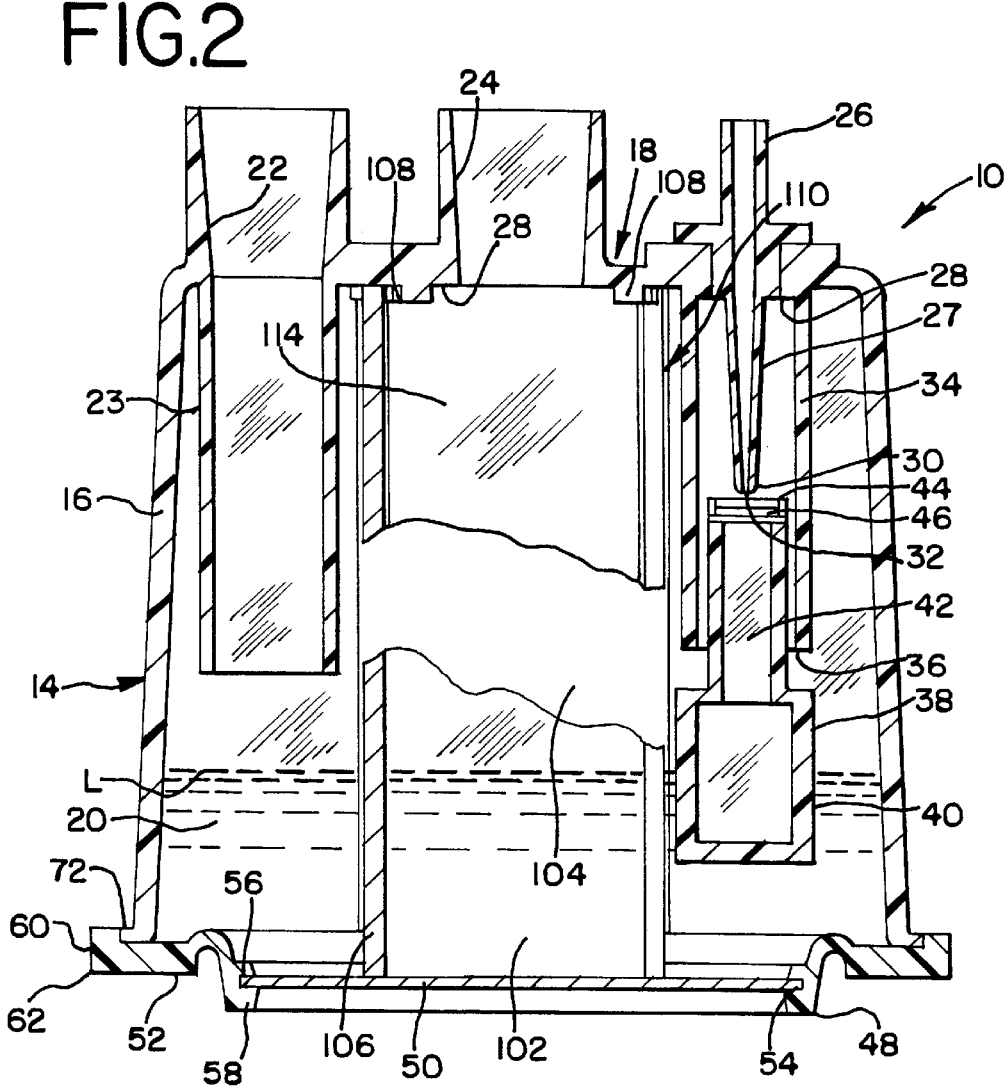
FIG. 2 is a cross-section taken along the line 2—2 of FIG. 1 and in the direction generally indicated.

Referring to FIGS. 1 and 2, an improved heater cartridge humidifier is shown and generally designated as 10, and is configured to be operationally engaged with a conventional heating unit, generally designated as 12. The humidifier cartridge 10 includes a humidifier housing 14 with a substantially vertical sidewall 16 and an upper end or top portion 18 integrally formed with the sidewall so as to define a humidifier chamber 20. Extending above and below the upper end portion 18 is a substantially cylindrical gas inlet 22 with a lower end 23. Appending from the upper end portion 18 is a substantially cylindrical gas delivery outlet 24. The gas inlet 22 and the gas delivery outlet 24 are adapted to be connected to a conventional breathable gas delivery system of the type used for respiratory patients. A nipple-like water inlet port 26, appending from the upper end portion 18, is adapted to be connected to a gravity feed collapsible water supply bag (not shown) as is well known in the art. The gas inlet 22, the gas delivery outlet 24 and the water inlet 26 are in fluid communication with the chamber 20.

In the preferred embodiment, the housing 14 is made of transparent plastic such as polystyrene. However, it is contemplated that other types of conventionally available self-supporting, sanitizable, inexpensive materials including polycarbonate, may be used to fabricate at least a portion of the housing. Also, while it is preferred that the inlets 22 and 26, and the outlet 24 are disposed on the upper end portion 18, it is also contemplated that these features may be located elsewhere on the housing, such as on the sidewall 16.

It is preferred that the water inlet 26 is in fluid communication with a water feed tube 27 depending from an underside 28 of the upper end portion 18. A lower end of the feed tube 27 includes nipple formation 30 with an axially disposed opening 32. A float retaining tube 34 depends from the underside 28 of the upper end portion 18 and circumscribes the water feed tube 27. The float retaining tube 34 includes a lower opening 36.

A float 38 is dimensioned to be slidingly retained in the lower end 40 of the float retaining tube 34. The float 38 is essentially a tube of water tight buoyant material with a generally larger diameter lower end 40. An upper end portion 42 of the float 36 has a relatively smaller diameter than the lower end 40 and has a recess 44 into which a disc or pad 46 of rubber or other resilient material is secured. The dimensions and material used for the pad 46 are such that upon contact with the nipple formation 30, the axial opening 32 will be sealed, effectively cutting off the flow of water from the water inlet 26.

Figure 3:
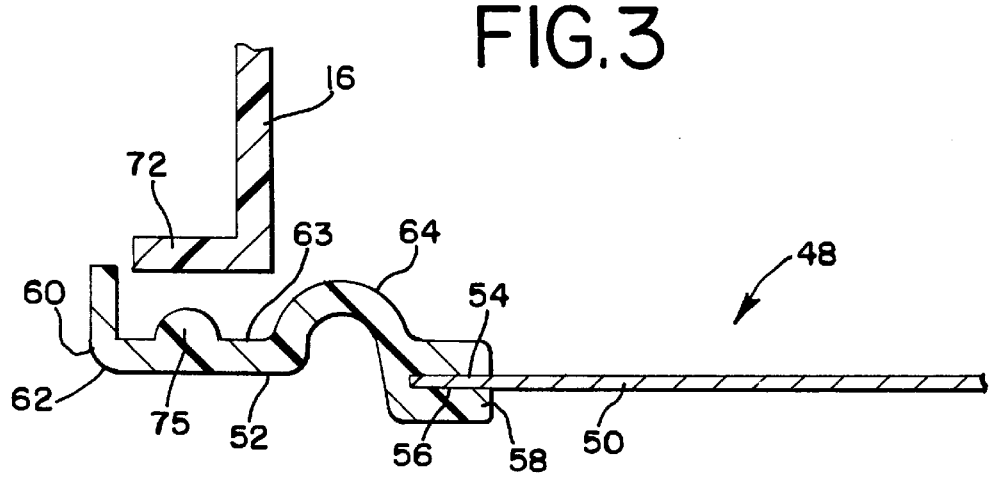
FIG. 3 is a fragmentary vertical cross-sectional view of the base plate for the present improved heated cartridge humidifier.

Referring now to FIGS. 2 and 3, the housing 14 is seated on a base plate 48 which includes a central conductive portion 50 and an insulating outer portion 52. A perimeter 54 of the central conductive portion 50 is sealingly retained within a groove 56 at an inner diameter 58 of the insulating portion 52. The central conductive portion 50 is preferably made of anodized aluminum but it is contemplated that other similar heat conductive materials would be equally useful. In the preferred embodiment, the conductive portion 50 is insert molded into the insulating portion 52. However, it is contemplated that alternative production techniques known to skilled practitioners may be utilized.

A peripheral lip 60 extends vertically from an outer diameter 62 of the insulating portion 52. In the preferred embodiment, the insulating portion 52 is made of a plastic material such as polycarbonate, however, other known suitable heat insulating plastic materials are contemplated. Between the inner diameter 58 and the outer diameter 62 is disposed an annular mating surface 63 and an annular, generally arcuately shaped support formation 64. As best seen in FIG. 1, the peripheral lip 60 is interrupted in a plurality of positions about the outer diameter 62 to form recesses or notches 68. The notches 68 include notch lips 70 which are essentially the same height as peripheral lips 60 but are positioned closer to the mating surface 63 than to the peripheral lip 60. In operation, the notches 68 are used for properly engaging the cartridge 10 to the heating unit 12, as described below.

Figure 4:
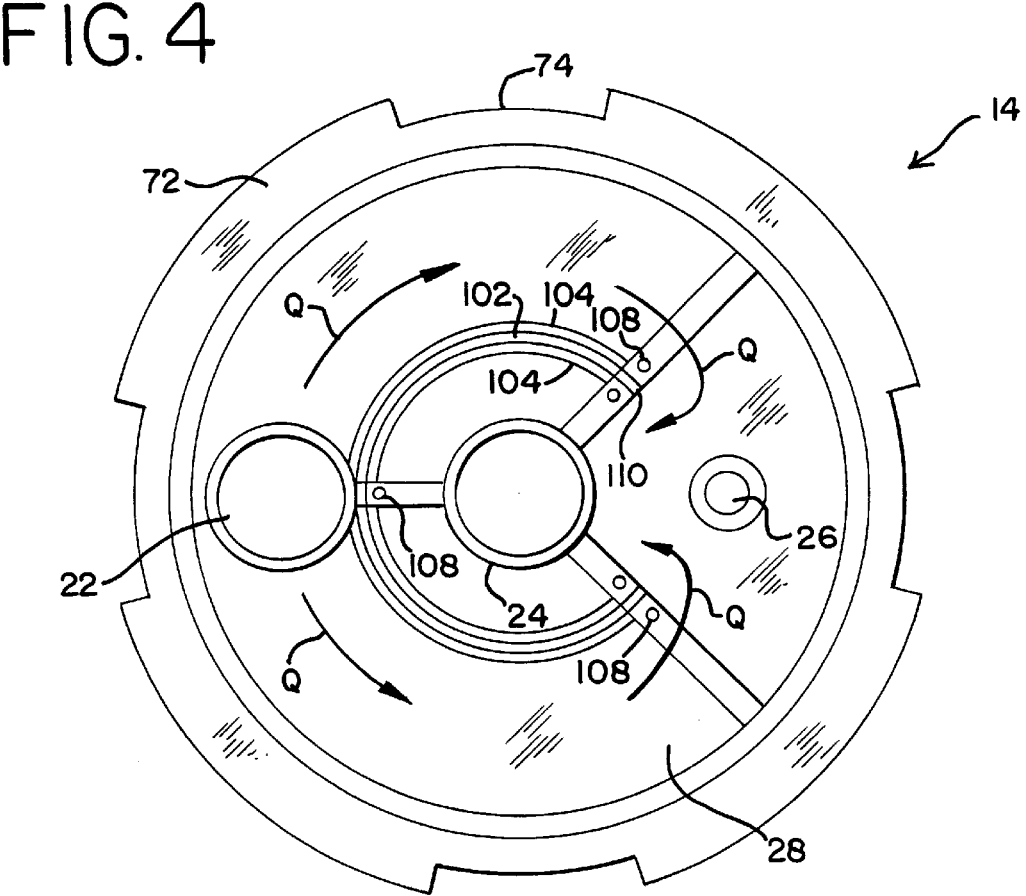
FIG. 4 is a bottom plan view of the cartridge housing of the present improved heated cartridge humidifier.

As shown in FIGS. 3 and 4, the lower end of the sidewall 16 of the housing 14 has a radially projecting flange 72 which forms the attachment point for the base plate 48. As best seen in FIG. 4, the flange 72 is interrupted in a plurality of positions by notches 74 which correspond to the notches 68 on the outer diameter 62 of the insulating portion 52. The mating surface 63 of the insulating portion 52 includes a plurality of knobs 75 spaced about the base plate 48. Once the flange 72 is seated on the mating surface 63, the mating surface and the flange are preferably ultrasonically welded together. The knobs 75 provide sufficient material to form an absolute bond between the flange 72 and the surface 63. However, it is also contemplated that suitable chemical adhesives may be used to sealingly fasten the base plate 48 to the housing 14.

Structural support is provided to the base plate 48 by the support formation 64. In addition, it has been found that the arcuate shape of the support formation 64 exerts a preload or hold down force on the conductive portion, which holds it down against the heating unit 12.

Referring now to FIG. 1, the heating unit 12 is designed to provide heat to the water delivered to the chamber 18 through the inlet 26 so that the water is more easily vaporized, and to provide water to a patient at a temperature which is as comfortable as possible. Included in the heating unit 12 is a housing 76 having a lower end 78 designed for positioning a substrate such as a shelf or a table, and an upper end 80. A control panel 82 is part of the heating unit 12 and is equipped with a temperature setting control 84 and various temperature warning lights and alarm indicators, generally designated as 86. A power switch 88, a power cord 90, and temperature sensor inputs 91 and 92 are preferably located on a panel 93 of the housing 76. The upper end 80 of the housing 76 has a heating surface 94 which is partially surrounded by a generally semicircular bracket 95. The bracket 95 is generally "C" or channel shaped in cross section to define an inwardly opening channel 96. A pivoting locking tab 98 is mounted to the upper end 80 of the housing 76 through use of a pivot member 100, which may be a pin or threaded fastener. The dimensions of the peripheral lip 60 and notch lip 70 of the base plate 48 are such that the cartridge 10 may be slid into the channel 96 to engage the bracket 95. The locking tab 98 is then moved to the vertical position as indicated in FIG. 1 to maintain the humidifier 10 in operational alignment upon the heating surface 94. In this position, the conductive portion 50 will be conductively heated by the heating surface 94.

In operation, water is supplied through the water inlet 26 by the use of a gravity feed supply as is well known in the art. As the water level 'L' (best seen in FIG. 2) within the chamber 20 rises, the float 38 rises until the disc 46 on the upper end portion 42 of the float 38 contacts the opening 32 of the feed tube 26 and effectively cuts off the flow of water into the housing 18. Breathable gases for treatment of patients enter the housing 14 through the gas inlet 22.

A feature of the present humidifier 10 is that the extended lower end 23 of the inlet 22 directs the gases to the area immediately above the surface 'L' of the water so that the gas is prevented from directly exiting through the outlet 24 without being properly humidified.

Heat generated by the heating surface 92 is transferred through the conductive portion 50 to heat the water in the chamber 20 to vaporize the water and warm the gases. As the respiratory gases flow through the heated and humidified chamber 20, the water level 'L' will fall due to evaporation. As the water level falls, the float 38 will also fall, pulling the disc 46 away from the feed tube opening 32 to allow the lost water to be replaced.

An important feature of the present humidifier 10 is that the conductive portion 50, being isolated from the sidewall 16 by the insulating portion 52, provides for superior heat transfer between the heating surface 92 and the water. The insulating portion 52 is dimensioned to separate the perimeter 56 of the conductive portion 50 from the sidewall 16 a sufficient distance to prevent the lateral dissipation of heat between the conductive portion and the sidewall. In this manner, heat is prevented from being dissipated to the ambient air, and is instead forced upward to warm the water. It has been found that the temperature of humidified gas measured at the outlet 24 is approximately 99° F., while prior art cartridges with totally conductive conventional base plates used at the same heater settings only produced humidified gas at 93° F. measured at the outlet 24.

Referring now to FIGS. 2 and 4, to enhance the evaporation of the water within the chamber 18, a partial sleeve 102, surrounded by a conventional paper-like wicking material 104, can be inserted in the chamber 20 generally underneath the gas delivery outlet 24. The sleeve 102 is preferably a rigid material such as aluminum and has a lower end 106 in contact with the conductive portion 50 of the base plate 48. A plurality of lugs 108 which are integrally formed with, and depend from the underside 28 of the upper end portion 18, provide the upper attachment point for the sleeve 102. It will be seen in FIG. 4 that the sleeve 102 is positioned within the chamber 20 to contact the gas inlet 22 at its apex. Also, an open portion 110 faces toward the float retaining tube 34.

In operation, the material 104 draws water from the lower portion to the upper portion of the chamber 20. The sleeve is preferably made of anodized aluminum to assist in conducting heat into the chamber 20 and for vaporizing the water on the wicking material 104. The disposition of the sleeve 102 within the chamber 20 causes incoming air to travel in the direction of the arrows Q around the perimeter of the housing 14, where it is humidified before it can exit the chamber through the opening 10 and, ultimately through the outlet 24.

Figure 5:
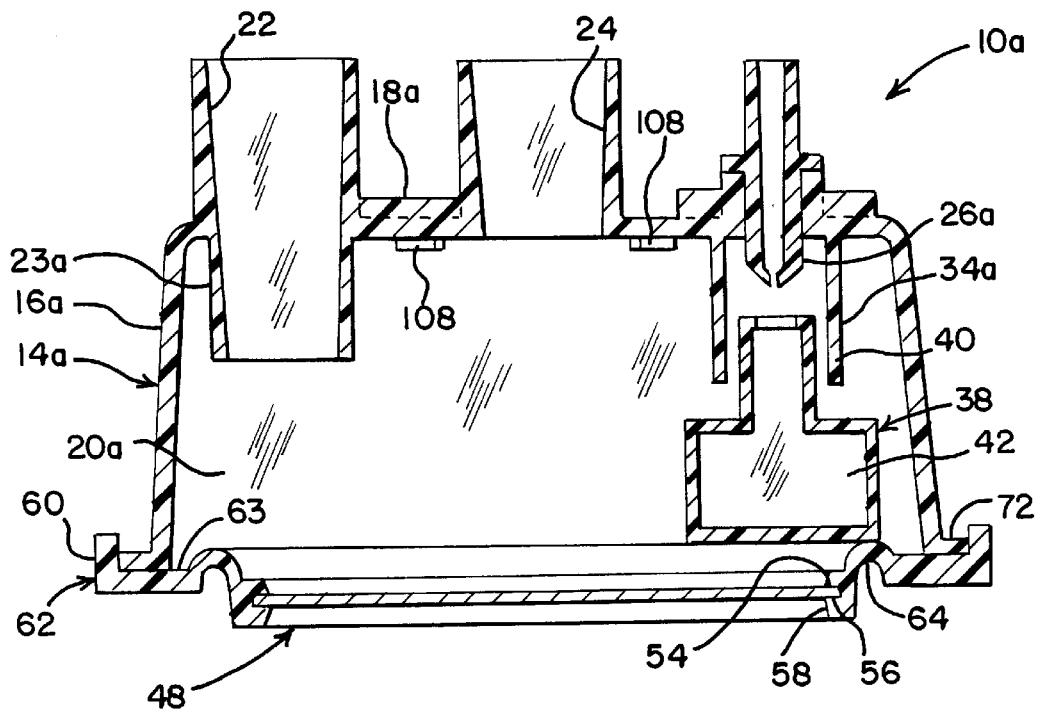
FIG. 5 is a vertical cross-section of an alternative embodiment of the present improved heated cartridge humidifier.

Referring now to the embodiment of FIG. 5, an alternate embodiment of the humidifier 10 is generally designated 10a, and is preferred for use in pediatric respiratory therapy. Many of the features of the cartridge 10a shown in FIG. 5 are identical to those of the cartridge 10 as described above and are indicated with identical reference numbers. In general, the cartridge 10a has been modified to provide for a smaller vaporization chamber 20a. It is believed that the smaller vaporization chamber 20a will prevent pediatric patients from becoming hyperventilated. The housing 14a has a sidewall 16a and an upper end portion 18a. The lower end 23a of the gas inlet 22a is relatively shorter than the lower end portion 23 of the gas inlet 22 of the housing 14 (FIG. 1). This accommodates the shorter sidewall 16a. Likewise, the feed tube 26a, the float retaining tube 34a and the upper end 40a and the lower end 42a of the float 38a are dimensioned to accommodate a smaller housing 14a. The base plate 48 is identical to that described above and it attaches to the housing 14a in identical fashion. Further, if desired, an appropriately dimensioned sleeve and wicking material (not shown) could be inserted into the chamber 18a and retained by the lugs 108. Operationally, the cartridge 110a works in an identical fashion as the cartridge 10 except the cartridge 110a has a smaller air and water volume.

It will be appreciated that a major advantage of the present heated cartridge humidifier is that the heating and humidification of respiratory gases can be readily accomplished. The seal between the humidifier housing is improved to prevent leaking while providing for an efficient transfer of heat between a heat source and the water. Another advantage of the present invention is that it provides for enhanced humidification of the breathable gas prior to transmittal to the patient.

While a particular embodiment of the improved heated cartridge humidifier of the invention has been shown and described, it will be appreciated by those skilled in the art that changes and modifications may be made thereto without departing from the invention in its broader aspects and as set forth in the following claims.

What is claimed:

1. A heated cartridge humidifier for use with a gravity feed water supply, a breathable gas supply and a separate heat source, and, when engaged with the heat source, the humidifier heating and humidifying the breathable gas to be inhaled by a patient, said humidifier comprising:

a humidifier housing that operationally engages the heat source for receiving heat therefrom, said housing having a sidewall with an open lower end portion and a closed upper end portion, said housing being provided with a gas inlet, a humidified gas outlet, and a water inlet adapted to receive water from the supply; and a base plate sealingly engaged to said open lower end of said housing, said base plate including an insulating portion and a conductive portion, said insulating portion sealingly retaining a perimeter of said conductive portion and providing the attachment point of said base plate to said housing, said conductive portion being made of a material which conducts heat received from the heating source for heating water received from said water inlet and humidifying the breathable gas.

2. The cartridge humidifier as defined in claim 1 wherein said insulating member is fabricated of plastic material and said heat conductive barrier member is metallic.

3. The cartridge humidifier as defined in claim 1 wherein said insulating portion laterally displaces said perimeter of said conductive portion from said sidewall for preventing a lateral dissipation of heat received from the heat source.

4. The cartridge humidifier as defined in claim 1 wherein said gas inlet further comprises an extended lower end depending from an underside of said upper end portion for directing the breathable gas toward the surface of the water in the cartridge for enhancing humidification of the gas.

5. The cartridge humidifier as defined in claim 1 further comprising a water feed tube extending into said housing.

6. The cartridge humidifier as defined in claim 5 further comprising a float retaining means circumscribing said water feed tube and having a portion configured for retaining a float therein, said feed tube being in fluid communication with said humidifier housing.

7. The cartridge humidifier as defined in claim 6 further comprising a float with an upper end portion slidingly retained in said float retaining means, said upper end portion sealingly engaging a lower end of said water feed tube so that the engagement of said float with said feed tube controls the flow of water into said humidifier housing.

8. The cartridge humidifier as defined in claim 7 wherein said upper end portion of said float has a pad of resilient material affixed thereto so as to sealingly engage the lower end of said water feed tube.

9. The cartridge humidifier as defined in claim 1 further comprising a wicking means for enhancing the evaporation occurring within said housing.

10. The cartridge humidifier according to claim 9 wherein said wicking means is a partial aluminum sleeve depending from an underside of said upper end portion and surrounded by a wicking material.

11. The cartridge humidifier as defined in claim 1 wherein said closed upper end portion is integrally formed with said sidewall.

12. An improved heated cartridge humidifier for use with a gravity feed water supply container and a separate heat source, the humidifier having a housing operationally engaging the heat source for receiving heat therefrom, said housing having a sidewall, an open lower end portion and an integrally formed closed upper end portion, said housing defining a chamber with a gas inlet, a gas outlet, a water inlet in fluid communication with water from the container, and a water control system for controlling the amount of water entering said chamber through said inlet, the improvement comprising a base plate including an insulating portion and a conductive portion, said insulating portion sealingly retaining a perimeter of said conductive portion, said insulating member being sealingly engaged to the open end portion of said housing.

13. The improved heated cartridge humidifier according to claim 12 wherein said gas inlet further comprises an extended lower end depending from an underside of said upper end portion for directing the breathable gas toward the surface of the water in the cartridge for enhancing humidification of the gas.

14. A heated cartridge humidifier for use with a gravity feed water supply, a breathable gas supply and a separate heat source, and, when engaged with the heat source, the humidifier heating and humidifying the breathable gas to be inhaled by a patient, said humidifier comprising:

a humidifier housing operationally engaging the heat source for receiving heat therefrom, said housing having a sidewall with an open lower end portion and a closed upper end portion, said housing being provided with a humidified gas outlet, a water inlet adapted to receive water from the supply and to retain said water at a specified level, and a gas inlet including an extended lower end depending from an underside of said upper end portion into said housing to a point adjacent the level of the water for directing the breathable gas adjacent the level of the water in the housing for enhancing humidification of the gas; and a base plate sealingly engaged to said open lower end of said housing.

15. The improved heated cartridge humidifier as defined in claim 14 wherein said base plate includes an insulating portion and a conductive portion, said insulating portion sealingly retaining a perimeter of said conductive portion and providing the attachment point of said base plate to said housing, said conductive portion conducting heat received from the heating source for heating water received from said water inlet and humidifying the breathable gas.

\* \* \* \* \*